(12) United States Patent
Bueno Melendo et al.

(10) Patent No.: US 8,063,079 B2
(45) Date of Patent: Nov. 22, 2011

(54) CYCLOPROPYL COMPOUNDS

(75) Inventors: Ana Belen Bueno Melendo, Madrid (ES); Francisco Javier Agejas-Chicharro, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 147 days.

(21) Appl. No.: 12/635,758

(22) Filed: Dec. 11, 2009

(65) Prior Publication Data

US 2010/0160395 A1 Jun. 24, 2010

Related U.S. Application Data

(60) Provisional application No. 61/153,781, filed on Feb. 19, 2009.

(30) Foreign Application Priority Data

Dec. 19, 2008 (EP) .................................. 08380341

(51) Int. Cl.
*A61K 31/427* (2006.01)
*C07D 417/12* (2006.01)
*A61P 3/10* (2006.01)

(52) U.S. Cl. ........................................ 514/369; 548/185

(58) Field of Classification Search .................. None
See application file for complete search history.

(56) References Cited

U.S. PATENT DOCUMENTS

2010/0056460 A1   3/2010   Ali et al.

FOREIGN PATENT DOCUMENTS

| WO | 0183465 | 11/2001 |
|----|---------|---------|
| WO | 0185706 | 11/2001 |
| WO | 0185707 | 11/2001 |
| WO | 2004063179 | 7/2004 |
| WO | 2004/072031 | 8/2004 |
| WO | 2004/072066 | 8/2004 |
| WO | 2005/103021 | 11/2005 |
| WO | 2006/016194 | 2/2006 |
| WO | 2006058923 | 6/2006 |
| WO | 2007007886 | 1/2007 |
| WO | 2007/051845 | 5/2007 |
| WO | 2007/051846 | 5/2007 |
| WO | 2007/051847 | 5/2007 |
| WO | 2009/133687 | 11/2009 |

OTHER PUBLICATIONS

Zhang, et al., "Benzamide derivatives as dual-action hypoglycemic agents that inhibit glycogen phosphorylase and activate glucokinase," Bioorganic & Medicinal Chemistry, vol. 17, pp. 7301-7312 (2009).

Wei, et al., "Effects of glucokinase activators GKA50 and LY2121260 on proliferation and apoptosis in pancreatic INS-1 beta cells," Diabetologia, vol. 52, pp. 2142-2150 (2009).

Efanov, et al., "A Novel Glucokinase Activator Modulates Pancreatic Islet and Hepatocyte Function," Endocrinology, vol. 146, No. 9, pp. 3696-3701 (2005).

Heuser, et al., "Synthesis of novel cyclopropylic sulfones and sulfonamides acting as glucokinase activators," Tetrahedron Letters, vol. 47, pp. 2675-2678 (2006).

*Primary Examiner* — Kamal Saeed
(74) *Attorney, Agent, or Firm* — James B. Meyers

(57) ABSTRACT

A compound of the formula:

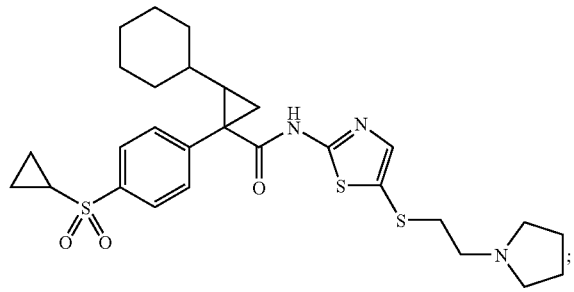

and pharmaceutical compositions for the treatment of diabetes.

8 Claims, No Drawings

CYCLOPROPYL COMPOUNDS

Diabetes is a progressive disease which adversely affects both longevity and quality of life. Existing oral therapies, either alone or in combination, do not exhibit adequate or sustained glucose lowering efficacy in patients with diabetes. Consequently, there is an unmet need for improved therapies for patients with diabetes.

Glucokinase activators (GKAs) represent a class of glucose-lowering agents which primarily act to lower blood glucose through modulatory actions in the pancreatic β-cells and the liver. A number of synthetic GKAs have been disclosed for the treatment of diabetes, for example those disclosed in WO 04/063179. There remains a need for alternative GKAs as therapy for patients with diabetes.

It has been shown that Glucokinase (GK) is critical for mediation of glucose sensing in neurons. GK activation in the hypothalamus dampens the counterregulatory response to insulin-induced hypoglycemia. Thus, activation of GK in the brain with GKA may produce an increased risk for hypoglycemia by decreasing secretion of epinephrine, norepinephrine, and glucagon levels at low glucose levels. GKA compounds with limited blood brain barrier permeability would have a lower potential for producing severe hypoglycemia.

The compounds of the present invention have been found to activate glucokinase both in vitro and in vivo. The compounds of the present invention have been found to exhibit improved potency over existing GKAs. The compounds of the present invention have been found to exhibit limited blood brain barrier permeability.

The present invention is directed to compounds which activate glucokinase, pharmaceutical compositions containing them as an active ingredient, methods for the treatment of disorders associated with glucokinase dysfunction, and to their use for the treatment of diabetes, in particular Type II diabetes.

The present invention provides a compound of the formula:

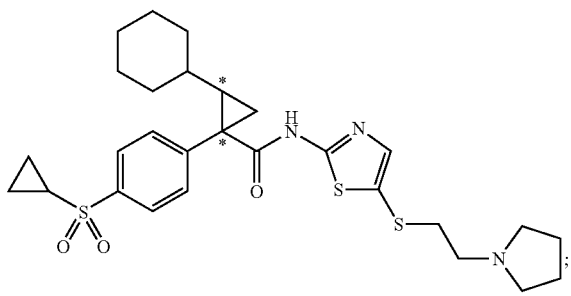

(I)

or a pharmaceutically acceptable salt thereof.

A compound of the present invention has two stereocenters (*) and thus four possible stereoisomers. It is intended that each stereoisomer and racemic or diastereomeric mixtures, whether pure or partially pure, are included within the scope of the invention.

A preferred stereoisomer of a compound of the present invention has the structural formula:

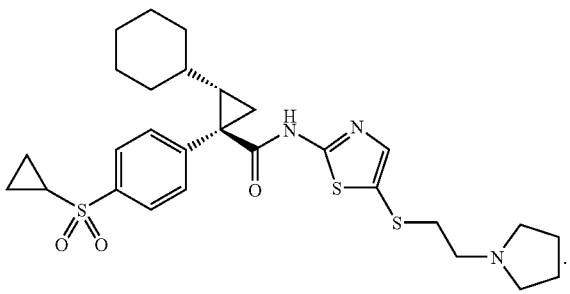

The present invention provides a pharmaceutical composition comprising a compound of the present invention, or a pharmaceutically acceptable salt thereof, and a pharmaceutically acceptable diluent or carrier.

The present invention provides a compound of Formula I, or a pharmaceutically acceptable salt thereof, for use in therapy. The present invention also provides a compound of Formula I, or a pharmaceutically acceptable salt thereof for use in the treatment of diabetes, in particular type II diabetes. In another aspect of the present invention, there is provided the use of a compound of Formula I, or a pharmaceutically acceptable salt thereof, for the manufacture of a medicament for the treatment of diabetes, in particular Type II diabetes.

The present invention provides a method for the treatment of diabetes, which comprises administering an effective amount of a compound of Formula I, or a pharmaceutically acceptable salt thereof, to a human being or animal in need thereof. The present invention also provides a method for the treatment of Type II diabetes, which comprises administering an effective amount of a compound of Formula I, or a pharmaceutically acceptable salt thereof, to a human being or animal in need thereof.

The present invention provides a pharmaceutical composition for use in therapy comprising a compound of the present invention, or a pharmaceutically acceptable salt thereof. The present invention provides a pharmaceutical composition for use in diabetes, in particular type II diabetes, comprising a compound of the present invention, or a pharmaceutically acceptable salt thereof.

As used herein the term "pharmaceutically acceptable salt" refers to salts of a compound of the present invention which are substantially non-toxic to living organisms. Such salts and common methodology for preparing them are well known in the art. See, e.g., P. Stahl, et al., Handbook of Pharmaceutical Salts: Properties Selection and Use, (VCHA/Wiley-VCH, 2002); and J. Pharm. Sci. 66, 2-19 (1977). A preferred pharmaceutically acceptable salt is hydrochloride.

The compounds of the present invention are preferably formulated as pharmaceutical compositions administered by a variety of routes. Most preferably, such compositions are for oral administration. Such pharmaceutical compositions and processes for preparing same are well known in the art. See, e.g., Remington: The Science and Practice of Pharmacy (A, Gennaro, et al., eds., 19$^{th}$ ed., Mack Publishing Co., 1995).

In a further aspect of the invention the present compounds are administered in combination with one or more active substances. Such active substances include for example metformin.

Administration in combination includes simultaneous, sequential or separate administration.

The compound names for the following example are generated using AutoNom 2000.

General Procedures:

All water- or air-sensitive reactions are conducted in dry solvents under an inert atmosphere. Mass spectra (MS) are obtained on an Agilent 1100 MSD spectrometer operating in electrospray mode. Optical rotations are obtained in chloroform on a JASCO DIP-370 digital polarimeter at 20° C. with a sodium D line.

EXAMPLE 1

(1R,2S)-2-Cyclohexyl-1-(4-cyclopropanesulfonyl-phenyl)-cyclopropanecarboxylic acid [5-(2-pyrrolidin-1-yl-ethylsulfanyl)-thiazol-2-yl]-amide

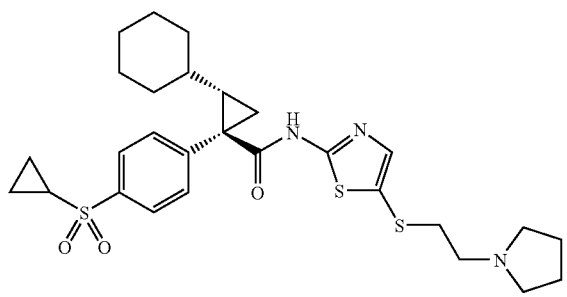

A) (4-Cyclopropanesulfonyl-phenyl)-diazo-acetic acid ethyl ester

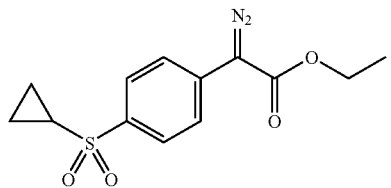

A mixture of (4-cyclopropanesulfonyl-phenyl)-oxo-acetic acid ethyl ester (250 g, 806 mmol) and p-toluenesulfonyl hydrazide (187 g, 984 mmol) in 1.5 L of ethanol is stirred at room temperature until a light yellow solution is obtained. Concentrated hydrochloric acid (20 mL, 233 mmol) is then added, and the resulting mixture is heated at reflux for 3.5 h. Volatiles are removed to provide a clear light yellow oil, which is dissolved in 1.5 L of ethyl acetate. This solution is then washed with 1 L of saturated aqueous sodium bicarbonate solution, followed by 1 L of saturated aqueous sodium chloride solution. The aqueous phases are back-extracted with ethyl acetate (2×500 ml), and the organic layers are combined, dried over magnesium sulfate, and filtered. This crude hydrazone solution (~2.1 L, assumed to contain 363 g of hydrozone intermediate) is stirred well while triethylamine (100 mL, 890 mmol) is added slowly. The resulting solution is left to stand overnight, during which time some solid precipitates. The mixture is diluted with ethyl acetate to a volume of 3 L, affording a solution, which is washed with 1 L of water, followed by two 500 mL portions of water combined with saturated aqueous sodium chloride solution as necessary to break up any emulsions. The resulting organic phase is then dried over magnesium sulfate, filtered, and concentrated to afford a damp solid, which is triturated with methyl t-butyl ether. The resulting slurry is filtered to afford a light yellow solid, which is dried under vacuum to afford 155 g of the title compound. The filtrate is concentrated to an oil, which is triturated as above until a free-flowing solid is obtained. This solid is isolated by filtration and dried to afford an additional 10 g of the title compound. LCMS (m/e): 295 (M+H).

B) (1R,2S)-2-Cyclohexyl-1-(4-cyclopropanesulfonyl-phenyl)-cyclopropanecarboxylic acid

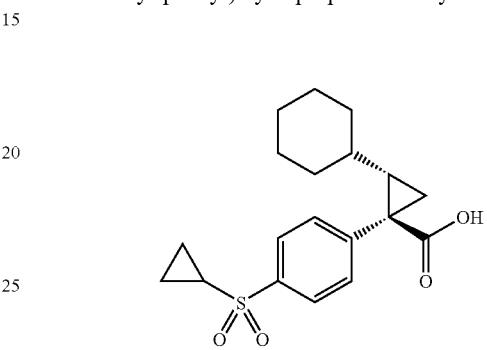

To a solution of vinylcyclohexane (300 mL, 2.72 mol) in 150 mL of anhydrous dichloromethane maintained at 25-30° C. under an inert atmosphere is added a solution of tetrakis [N-phthaloyl-(R)-tert-leucinato]dirhodium bis(ethylacetate) adduct (120 mg, 84 µmol) in vinylcyclohexane (40 mL) dropwise, while portions of (4-cyclopropanesulfonyl-phenyl)-diazo-acetic acid ethyl ester (169.40 g, 575.5 mmol) are added. The addition rates are adjusted to maintain an internal temperature of 40° C. The addition is complete after approximately 1.5 hours, and the reaction mixture is stirred for an additional 2 hours at 30° C. Volatiles are then removed under vacuum to afford crude (1R,2S)-2-cyclohexyl-1-(4-cyclopropanesulfonyl-phenyl)-cyclopropanecarboxylic acid ethyl ester as a viscous brown oil (218 g, 579 mmol) which is dissolved in 1.1 L of methanol to afford a yellow-brown solution, to which a 5 N aqueous sodium hydroxide solution (500 mL, 2.5 mmol) is added slowly. The resulting slurry is then stirred at 50° C. for 1 hour, during which time a solution forms. Methanol is removed under vacuum, and 1 L of ethylacetate is added. The resulting mixture is acidified by the addition of approximately 550 mL of 5% aqueous hydrochloric acid, and the two layers are separated. The aqueous layer is then extracted with two 500 mL portions of ethyl acetate. The organic phases are combined, washed with 500 mL of saturated aqueous sodium chloride solution, dried over magnesium sulfate, filtered, and concentrated to afford a moist pale yellow solid. This material is then dissolved in 1 L of methanol. Water (1 L) is then added to the stirred solution over the course of 1.5 hours. The resulting slurry is stirred at room temperature for 30 minutes, and then filtered. The filter pad is washed with 1:1 methanol/water, and dried to afford the title compound as pale yellow crystals (166 g). MS exact mass calculated 349.14735; found 349.14679 (Agilent 1100 LC-TOF using electrospray ionization); $[\alpha]_D^{20} = -31°$.

The enantiomeric excess of the acid is determined to be 97.7% by comparison of the integrals for the two peaks corresponding to the enantiomers as separated by chiral chromatography on an AD-H column (150 mm) eluted at 35° C. with 10% ethanol in hexanes containing 0.05% trifluoroacetic acid.

C) 5-(2-Pyrrolidin-1-yl-ethylsulfanyl)-thiazol-2-ylamine

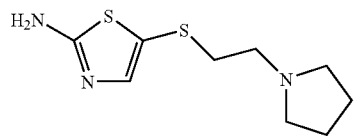

Thiirane (550 mL, 9.2 mol) is added to a mixture of pyrrolidine (543 mL, 6.57 mol) in 2.5 L of anhydrous dioxane under an inert atmosphere. The temperature rises slowly, and the reaction mixture is cooled in an ice bath when the internal temperature reaches 54° C. Once the temperature has dropped to 45° C., the cooling bath is removed and the reaction mixture is heated to 60° C. After 3 hours, the mixture is cooled to room temperature and concentrated under vacuum. The residue is then distilled at 6 mm Hg, and a fraction boiling at 50° C. is collected to afford 2-pyrrolidin-1-yl-ethanethiol as a colorless oil (643 g). MS (m/e): 132 (M+H).

Sodium bicarbonate ((1.232 kg, 14.7 mol) is added slowly in portions to a mixture of 5-bromo-thiazol-2-ylamine hydrobromide (1.53 Kg, 5.87 mol) in 7.5 L of isopropanol. 2-Pyrrolidin-1-yl-ethanethiol (1.060 Kg, 8.07 mol) is then added over 15 min, and the resulting mixture is stirred at 60° C. for 96 h. The temperature is increased to 70° C. for 1 h, and then the mixture is cooled to room temperature. Most of the isopropanol is removed under vacuum, and the residue is taken up in 4 L of an isopropanol/chloroform solution (1:9). Saturated aqueous sodium bicarbonate (4 L) is added, and the resulting mixture is stirred for 30 minutes. The layers are separated and the aqueous phase is extracted with three 4 L portions of an isopropanol/chloroform solution (1:9). The organic layers are combined, dried over sodium sulfate, filtered, and concentrated under vacuum. The resulting residue is triturated with 3 L of diethylether, and filtered off to give a first portion of the title compound as a pale-yellow solid (410 g). The filtrate is concentrated to an orange solid, which is triturated with 2 L of diethylether, and isolated as a beige solid by filtration. This solid is then dissolved in 2 L of methanol, and the solution is heated at 45° C. for 30 min. Upon cooling to room temperature, a solid is formed. This material is isolated by filtration, triturated with diethyl ether as above, and dried under vacuum to afford an additional 310 g of the title compound. MS (m/e): 230 [M+H]

D) (1R,2S)-2-Cyclohexyl-1-(4-cyclopropanesulfonyl-phenyl)-cyclopropanecarboxylic acid [5-(2-pyrrolidin-1-yl-ethylsulfanyl)-thiazol-2-yl]-amide Oxalyl chloride (146.89 mL, 1.69 mol) is added over 15 min to a stirred solution of (1R,2S)-2-cyclohexyl-1-(4-cyclopropanesulfonyl-phenyl)-cyclopropanecarboxylic acid (295.00 g, 0.847 mol) in 10 L of anhydrous dichloromethane under an inert atmosphere. Dimethylformamide (654.61 μL, 8.5 mmol) is then added at once, and the resulting solution is stirred overnight. Volatiles are then removed under vacuum at 40° C. to afford an oil, which is dissolved in 3 L of anhydrous dichloromethane. An inert atmosphere is reestablished, and the solution is cooled to <5° C. Triethylamine (177 mL 1.27 mol) is then added dropwise over 20 minutes, leaving a dark solution. Sodium Sulfate (120.25 g, 0.847 mol) is added, followed by 5-(2-pyrrolidin-1-yl-ethylsulfanyl)-thiazol-2-ylamine (213.60 g 0.931 mole). The internal temperature rises to 20° C. The reaction mixture is stirred for 10 min in the cold, and is then allowed to warm to room temperature. After being stirred overnight, the reaction mixture is poured onto 3 L of water. The resulting mixture is stirred for a few minutes, and then the two layers are separated. The aqueous layer is extracted with 1 L dichloromethane, and the dichloromethane solutions are combined, dried over $MgSO_4$, filtered, and concentrated under vacuum at 40° C. The resulting oil (556 g) is applied to silica gel plugs as a dichloromethane solution. Elution of the plugs with 1:12:7 2M ammonia in methanol/methyl t-butyl ether/heptane, followed by 1:19 2M ammonia (in methanol)/ethyl acetate affords a brown foam (351 g). Crystallization of 320 g of this material from methyl t-butyl ether and heptane, affords the title compound (279.4 g) as an off-white solid after drying for 2 days at 45° C. LCMS (m/e): 560 (M+H); $[\alpha]_D^{20} = -44°$.

Glucokinase Assay

The human islet GK isoform is expressed in *E. coli* as $(His)_6$-tagged fusion protein and purified with metal chelate affinity chromatography, see e.g. Tiedge et al., Biochem. Biophys. Acta 1337, 175-190, 1997. After purification the enzyme is stored in aliquots at concentration 0.8 mg/ml in 25 mM sodium phosphate, 150 mM sodium chloride, 100 mM imidazole, 1 mM dithiothreitol, 50% glycerol at −80° C. The assay is performed in flat bottom 96-well plates in a final incubation volume of 100 μL. The incubation mixture consists of 25 mM 4-(2-hydroxyethyl)-1-piperazineethanesulfonic acid (HEPES) (pH7.4), 50 mM potassiumchloride, 2.5 mM magnesiumchloride, 2 mM dithiothreitol, 4 U/ml glucose-6-phosphate dehydrogenase from *Leuconostoc mesenteroides*, 5 mM ATP, 1 mM NAD and a set concentration of glucose. Test compounds are dissolved in dimethylsulfoxide and then added to the reaction mixture giving the final dimethylsulfoxide concentration of 10%. The reaction is initiated by addition of 20 μL GK and run for 20 min at 37° C. The amount of formed NADH is measured as an increase in absorbance at 340 nm using a microplate reader. Absorbance values are used for $EC_{50}$ calculations.

Example 1 activated GK with an $EC_{50} = 42 \pm 42$ nM (n=5) at 10 mM glucose. It also increased the enzyme activity in a concentration dependent manner at lower glucose concentrations.

Glycolysis Assay

Rat insulinoma INS-1E cells are maintained at 37° C., 5% $CO_2$, 95% humidity in 1640 medium supplemented with 11 mM glucose, 5% Fetal Bovine Serum, 50 μM 2-Mercaptoethanol, 1 mM pyruvate, 10 mM HEPES and antibiotics. Prior to assay, cells are trypsinized, pelleted by centrifugation and seeded into 96-well tissue culture assay plates at the density of 30,000 cells/well. Cells are allowed to attach and incubated for 48 hours at 37° C., 5% $CO_2$. On the assay day, cells are washed with and incubated in 200 μL Earle's Balanced Salt Solution (EBSS) buffer supplemented with 0.1% Bovine Serum Albumin (BSA). After 30 minutes incubation, the buffer is removed and 100 μL EBSS buffer containing 0.1% BSA, 8 mM glucose and the compound is added to cells. Immediately after, 20 μL of CellTiter 96® AQueous One Solution Reagent is added to cells and cells are incubated at 37° C. for an additional hour. At the end of incubation absorbance at 490 nm is read. Absorbance values are used for $EC_{50}$ calculations.

Example 1 stimulates glucose metabolism in rat insulinoma INS1-E cells (mean $EC_{50}$=579±139 nM, n=4).

Thus, the compounds of the present invention are shown to activate GK in vitro.

Oral Glucose Tolerance Test(OGTT)

Male Wistar rats at a weight of 225-250 g, are kept on regular diet and with normal light cycle and conditions. For the study, rats are fasted overnight before their exact weights are measured, and are randomized into groups of similar weights (n=4 per group). The compound is suspended in a 1:1 mixture of solutol/ethanol in a bath sonicator (10% of total volume). The obtained suspension is then diluted with 9 volumes of 10% aqueous solutol solution, and the compound is dosed orally at 1, 3, 6, 10, 20, and 30 mg/kg orally. Rats are given a 2 g/kg oral glucose bolus 2 hours after compound administration. Blood is collected via tail bleed at 0, 15, 30, 60, 90 and 120 minutes post glucose administration. Collected blood is placed into ethylenediaminetetraacetic acid (EDTA) tubes at volume of 400 µL per sample, and the samples are kept on ice. Plasma is isolated and stored at −20° C. until samples are analyzed for glucose and compound exposure. Area under the plasma glucose curve (glucose AUC) is calculated for each group and the percentage decrease in the glucose AUC versus the control group is used as a measure of efficacy of the compound to decrease plasma glucose.

Example 1 decreases plasma glucose in a dose-dependent manner at both fasted and postprandial glucose levels. A maximal lowering of glucose AUC versus the untreated control group is observed with the high dose (30 mg/kg) and represents a 42% decrease. Interpolation of the data showed that a 20% glucose AUC decrease occurs at an average compound concentration of 99 ng/ml (179 nM) in plasma, corresponding to a 6.9 mg/kg compound dose.

Thus, the compounds of the present invention are shown to activate GK in vivo.

Blood Brain Barrier Permeability

A stock compound solution is prepared in dimethylsulfoxide at 10 mM. A dose solution is then prepared at 1 mM by diluting 100 µL of the stock with 900 µL of propylene glycol. The dose is administered as an IV bolus (2.2 mL/kg) via the tail vein into six male CF-1 mice (approximately 23 g) for a target dose of 2.17 µmole/kg. Mice are euthanized using both $CO_2$ and cervical dislocation. Three mice are sacrificed 5 minutes post dose and three 60 minutes post dose. Blood is collected from each animal via cardiac puncture, and plasma is prepared using sodium EDTA, transferred into polypropylene sample tubes and immediately frozen using dry ice. Complete brain is collected from each animal and bissected medially, each half being transferred into polypropylene sample tubes and immediately frozen using dry ice. Plasma samples are prepared for analysis by precipitation of protein using two parts of extraction solvent (10% tetrahydrofuran in acetonitrile) to one part plasma and mixing with a vortex mixer. For brain tissue, it is assumed that 1 mg brain tissue≈1 µL volume and two parts of extraction solvent are added to one part tissue. The samples are immediately homogenized using an ultrasoinc cell dismemberator. Calibration standards are prepared by spiking known concentrations of compound into blank mouse plasma and then treated as plasma samples.

All samples are centrifuged at 6000 RCF for 5 minutes. An aliquot of supernatant from each sample is transferred to a polypropylene 96 well plate and sealed for analysis by LC-MS/MS.

MS/MS is effected using a Sciex API 4000 triple quadrupole mass spectrometer equipped with a turbo ion spray source. High Performance Liquid Chromatogaphy is effected using a Phenomenex Hyrdro RP analytical column (100×2.0 mm, 4µ) heated to 50° C. and operated at a constant flow rate of 0.6 mL/minute. A mobile phase gradient is utilized consisting of an initial mobile phase of 60:40 5 mM aqueous ammonium formate:5 mM ammonium formate in methanol with a hold time of 1 minute followed by a linear 2 minute gradient to 10:90 5 mM aqueous ammonium formate:5 mM ammonium formate in methanol with a final hold time of 1 minute. Column effluent is diverted to waste from 0-2.8 minutes and then directed into the mass spectrometer from 2.8-4.0 minutes MS/MS transitions monitored are 560/84. Quantitation of compound in test samples is achieved by comparing peak area values to a quadratic equation weighted $1/x^2$ derived from the nominal concentrations of the calibration standards and their respective peak areas. Upper and Lower Limits of Quantitation are determined by the back calculated recoveries of calibration standards that exceeded +/−20% of theory. Brain tissue concentrations are corrected for plasma contribution using a literature factor of 16 µL of plasma/gm mouse brain.

The in vivo blood brain barrier permeability of Example 1 resulted in a mean brain/plasma ratio of 0.17 five minutes post dose and a mean total brain level of 0.539 nmol/g at that time.

The compounds of the present invention have been shown to have limited blood brain barrier permeability and so provides limited potential for severe hypoglycaemia.

We claim:
1. A compound of the formula:

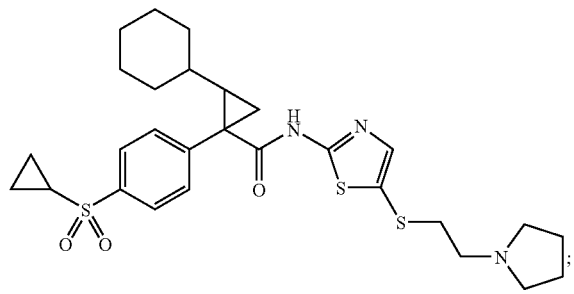

or a pharmaceutically acceptable salt thereof.

2. A compound according to claim 1 of the formula:

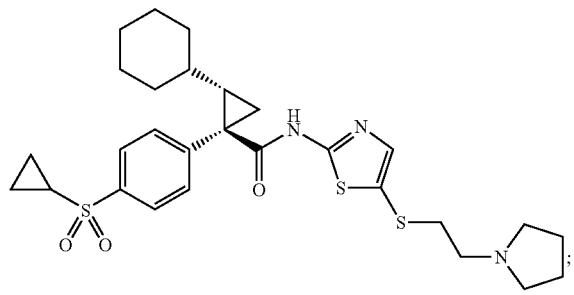

or a pharmaceutically acceptable salt thereof.

3. A pharmaceutical composition comprising a compound according to claim 1, or a pharmaceutically acceptable salt thereof, and a pharmaceutically acceptable diluent or carrier.

4. A pharmaceutical composition comprising a compound according to claim 2, or a pharmaceutically acceptable salt thereof, and a pharmaceutically acceptable diluent or carrier.

5. A method for the treatment of diabetes, which comprises administering an effective amount of a compound according to claim 1, or a pharmaceutically acceptable salt thereof, to a human being or animal in need thereof.

6. A method for the treatment of diabetes, which comprises administering an effective amount of a compound according to claim 2, or a pharmaceutically acceptable salt thereof, to a human being or animal in need thereof.

7. A method according to claim 5 for the treatment of type II diabetes.

8. A method according to claim 6 for the treatment of type II diabetes.

* * * * *